(12) United States Patent
Philpott

(10) Patent No.: US 6,843,432 B1
(45) Date of Patent: Jan. 18, 2005

(54) PERSONAL HYGIENE CLEANSING APPARATUS

(76) Inventor: Robert L. Philpott, 206 W. Church St., St. Marys, GA (US) 31558

( * ) Notice: Subject to any disclaimer, the term of this patent is extended or adjusted under 35 U.S.C. 154(b) by 5 days.

(21) Appl. No.: 09/716,131

(22) Filed: Nov. 17, 2000

(51) Int. Cl.[7] ............................................... B05B 15/00
(52) U.S. Cl. ........................ 239/289; 239/442; 239/526
(58) Field of Search ................................. 239/289, 397, 239/390, 413, 442, 444, 526, 525

(56) References Cited

U.S. PATENT DOCUMENTS

| | | | | |
|---|---|---|---|---|
| 1,328,650 A | * | 1/1920 | Donovan | 239/553.3 |
| 1,582,225 A | * | 4/1926 | Pulkinghorn | 422/266 |
| 1,746,422 A | * | 2/1930 | Gorham | 4/644 |
| 2,200,503 A | * | 5/1940 | Judell et al. | 4/653 |
| 2,266,902 A | * | 12/1941 | Perkins | 137/343 |
| 2,508,958 A | * | 5/1950 | Manville | 401/46 |
| 2,540,064 A | * | 1/1951 | Weber | 137/888 |
| 2,584,943 A | * | 2/1952 | Thomas | 239/458 |
| 2,624,619 A | * | 1/1953 | Fletcher et al. | 239/310 |
| 2,716,544 A | * | 8/1955 | Exley, Jr. et al. | 366/177.1 |
| 2,767,019 A | * | 10/1956 | Manville | 239/416.2 |
| 3,131,868 A | * | 5/1964 | Coleman | 239/455 |
| 3,498,546 A | * | 3/1970 | Logan et al. | 239/583 |
| 3,581,998 A | * | 6/1971 | Roche | 239/415 |
| 4,173,325 A | * | 11/1979 | Petrovic | 248/81 |
| 4,817,218 A | * | 4/1989 | Dimitriu et al. | 4/515 |
| 5,662,276 A | * | 9/1997 | Ko | 239/571 |
| 5,716,005 A | * | 2/1998 | McMahan | 239/315 |
| 6,322,005 B1 | * | 11/2001 | Kern et al. | 239/444 |
| 6,370,713 B2 | * | 4/2002 | Bosio | 4/677 |

* cited by examiner

*Primary Examiner*—Christopher Kim
(74) *Attorney, Agent, or Firm*—Rigdon Patents & Engineering, P.C.; Jonathan R. Smith

(57) ABSTRACT

A personal hygiene cleansing apparatus for use on the toilet is connected to hot and cold water supply lines in a bathroom. The water flows from these lines to a manually-controlled mixer for temperature control and then delivered to a hand-held spray gun. The apparatus may be built in to a wall or vanity, or it may be installed in a case for portability. Optionally, the apparatus comprises a soap tank which mixes soap with a portion of the incoming water for controlled application with the spray gun.

7 Claims, 5 Drawing Sheets

US 6,843,432 B1

PERSONAL HYGIENE CLEANSING APPARATUS

BACKGROUND OF THE INVENTION

It is commonplace in developed countries to cleanse one's nether body parts with either bathroom tissue or a bidet, or both, after using the toilet. The problem with tissue alone is that sometimes it is not sufficient to cleanse completely enough to suit the user. The problems with the bidet, on the other hand, are plumbing cost and space requirements for installation. The present invention provides the same or greater cleansing thoroughness of the bidet at significantly less cost and essentially no additional required space.

SUMMARY OF THE INVENTION

The present invention is a cleansing apparatus to connect to existing hot and cold water supply lines in a bathroom, that would be either built into a wall or vanity, hung on or hinged to a vertical surface, or made portable in either a cart or carrying case. The apparatus comprises means for mixing the hot and cold water and conveying the water stream to a hand-held sprayer having a built-in control valve. Means are also provided, optionally, for adding soap solution to the stream. The invention also provides a bracket for holding the spray head when it is not in use. The invention also comprises alternative sprayer heads which can be attached to, or substituted for, each other by the user or by multiple users.

Objects of this invention are to provide: a) a space- and money-saving alternative to a bidet for personal hygiene cleansing; b) a discreet and unobtrusive personal hygiene cleansing apparatus; c) a portable apparatus for personal hygiene cleansing; d) a personal hygiene apparatus that can be used with interchangeable spray heads; e) a personal hygiene cleansing apparatus that will add soap or other additives to the water conveniently and at the user's discretion.

DETAILED DESCRIPTION OF THE INVENTION

Figure 1:
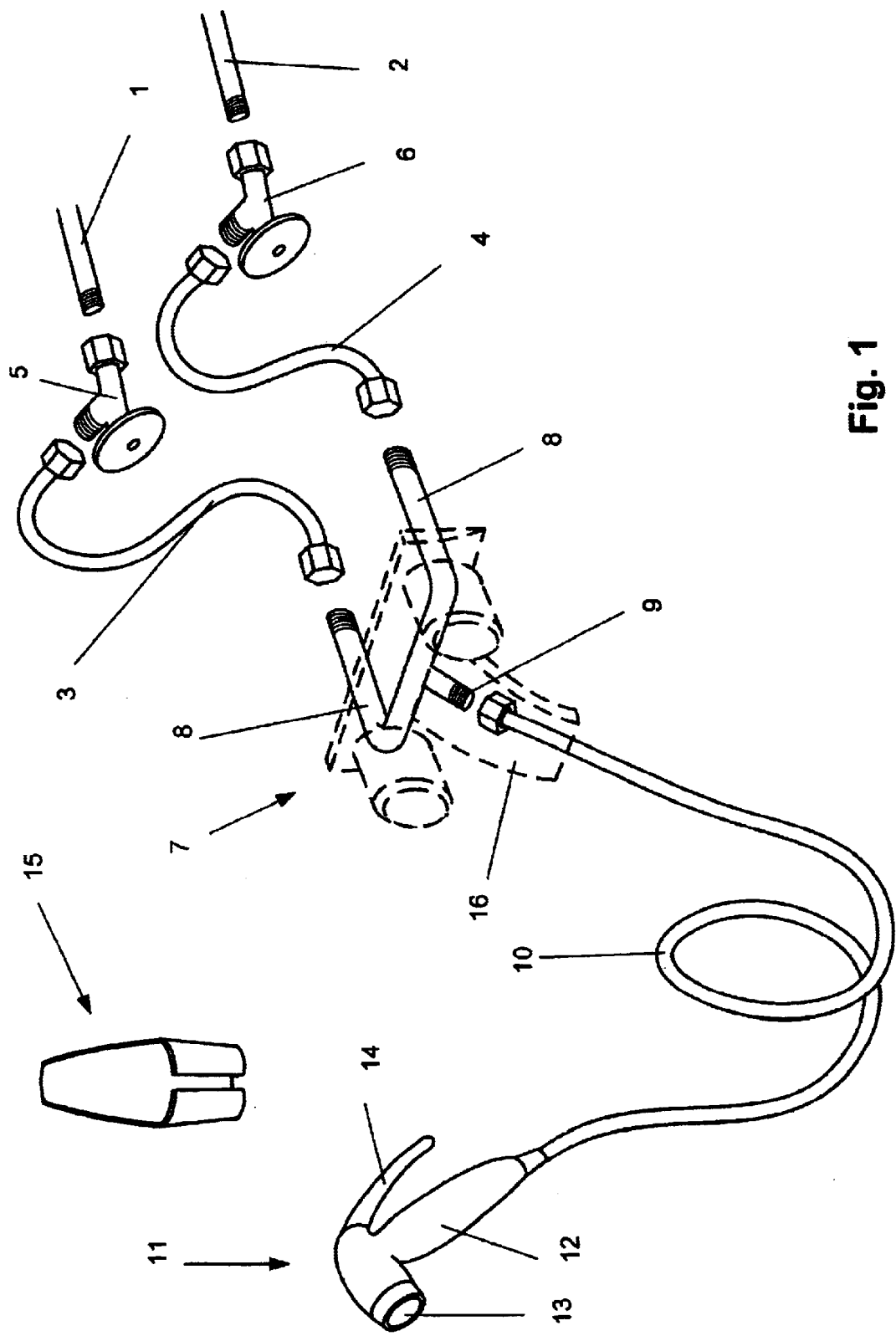
FIG. 1 is an exploded view of a first generic embodiment of the invention.

Referring now in detail to the drawings, in which like numerals depict like features in all drawings:

FIG. 1 is an exploded view of a first embodiment of the invention. A hot water supply line 1 and a cold water supply line 2 are connected to a hot water tube 3 and a cold water tube 4 respectively, either directly or through isolation valves 5 and 6. The tubes 3 and 4 are connected in turn to a mixer 7, containing one or more mixer valves 8 capable of being manually adjusted to control the proportions of hot and cold water fed through the invention and thereby the temperature of the water. FIG. 1 shows two valves with separate valve bodies, but the valve bodies may be combined into a single body with multiple flow paths. The configuration of the mixer is not important as long as the mixer is capable of controlling the individual proportions of the hot and cold water. The mixer outlet 9 is connected to a flexible hose 10, which in turn is connected to a hand-held spray gun 11. The spray gun 11 comprises a valve body 12, a spray head 13 and a valve handle 14 that is spring-biased and normally closed. Once the temperature of the water is adjusted to a satisfactory level by adjusting the mixer valve or valves 8, pressing the handle 14 opens the valve body 12 and allows properly attemperated water to emerge from the spray head 13 for application to a user's body. A bracket 15, attachable to a vertical surface and shaped to hold valve body 12 when not in use, may be provided. The mixer 7 may be built into a generic faucet assembly 16, shown here as environmental structure.

Figure 2:
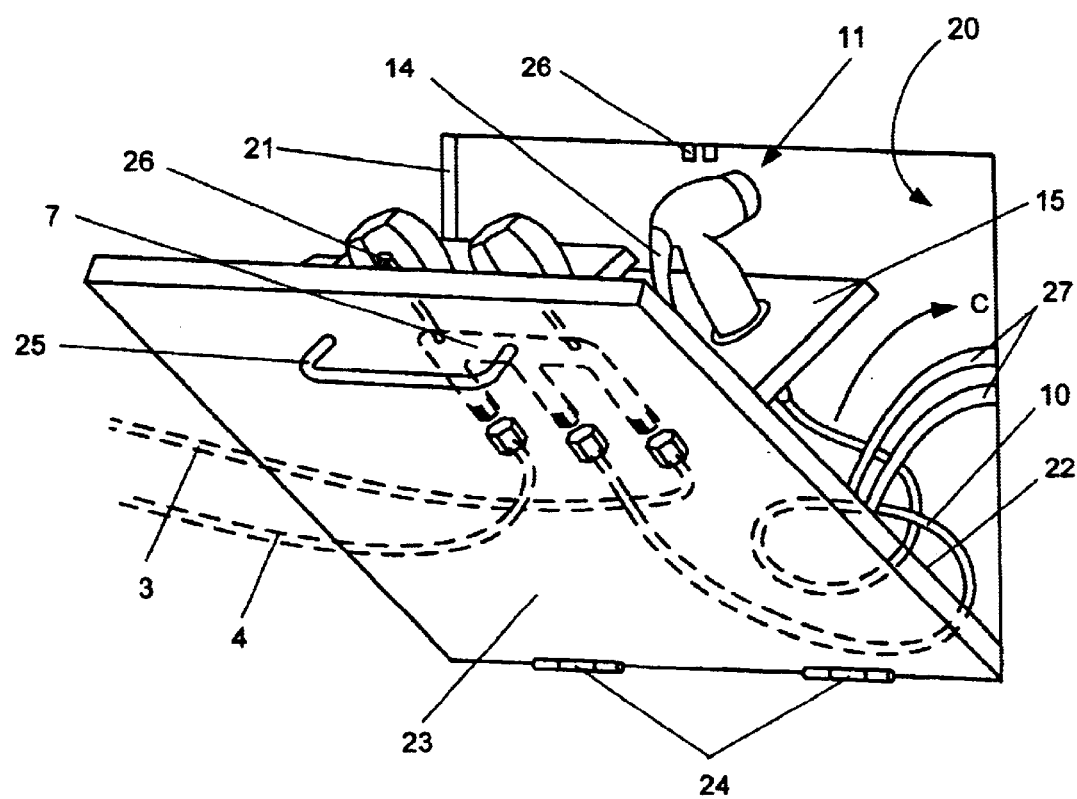
FIG. 2 is an exploded view of a second, built-in, embodiment of the invention.

FIG. 2 is a perspective view of a second, built-in, embodiment of the invention. In this embodiment, hot and cold water tubes 3 and 4 come from isolation valves 5 and 6 (not shown) within a space 20 fronted by a vertical panel 21. The sides of a rectangular cabinet or vanity, and the wallboard of a hollow wall, are examples of such vertical panels fronting spaces within which this embodiment may be built. Mixer 7 and bracket 15 are mounted on the inside surface 22 of a door 23, which is attached by hinges 24 to vertical panel 21, and may be opened outwardly by pulling on door handle 25. The extreme positions of door 23 may be delimited by latch 26 and rail assembly 27. A user seated on a toilet nearby may access the invention by pulling door 23 open and pulling spray gun 11 upwardly through bracket 15, and then by extending hose 10 sufficiently to reach into a position directing water into the toilet. By pressing valve handle 14, water can be sprayed into the toilet and tested for the proper temperature. The temperature can be adjusted as desired by adjusting mixer 7. Then the spray gun 11 can be pointed toward the user's body and the flow and force of the water stream controlled by the valve handle 14 to clean the body completely and comfortably. After use, the valve handle 14 is released, stopping the flow of water, and the user can dry off the spray gun 11 with tissue and return it to its bracket 15. When the door 23 is closed in the direction of arrow C, the invention is hidden from view by the door 23 and vertical panel 21 and protected from dust.

Figure 3:
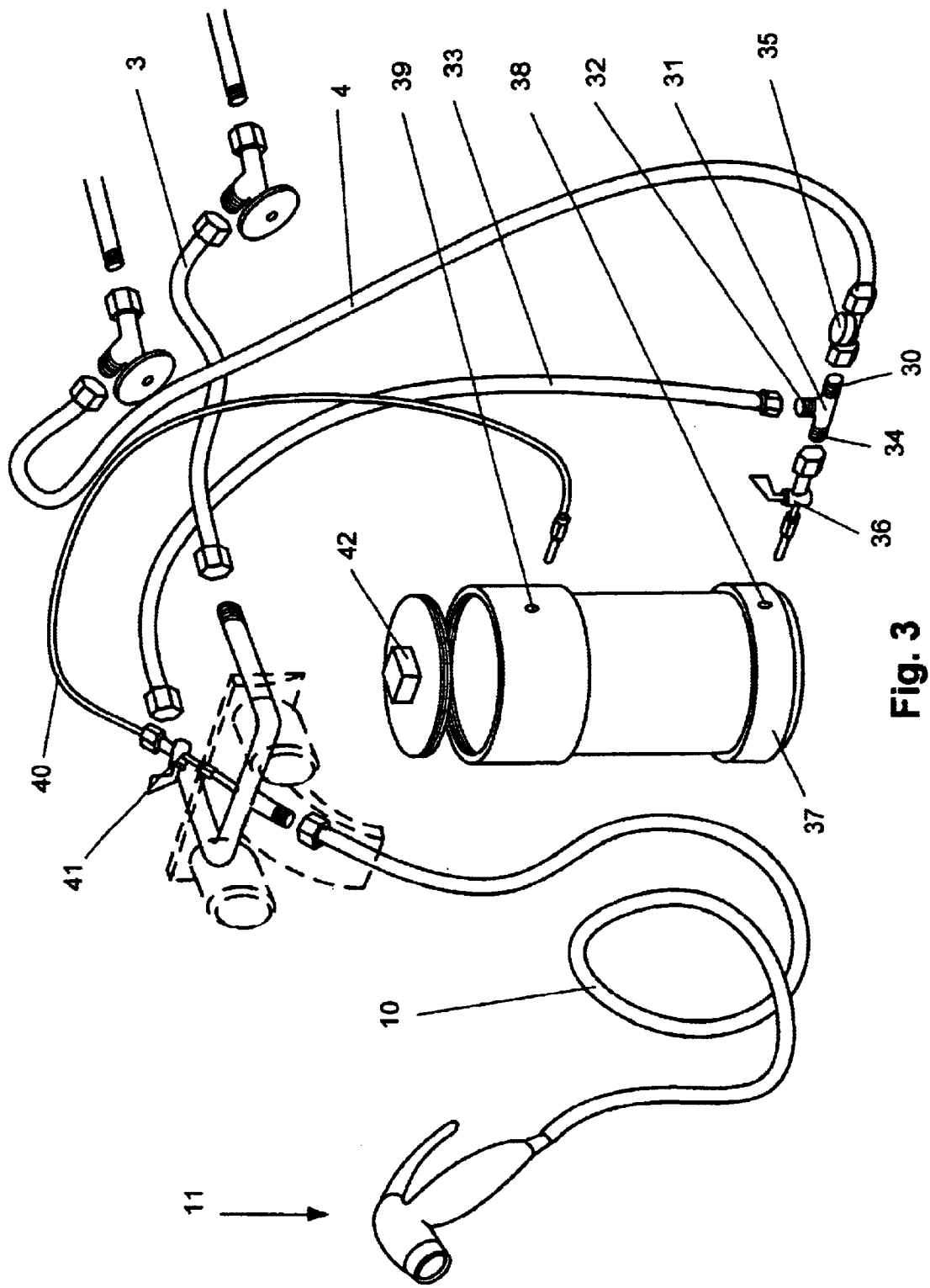
FIG. 3 is an exploded view of a third, soap-applying, embodiment of the invention.

FIG. 3 is an exploded view of a third, soap-applying, embodiment of the invention. In this embodiment, cold water tube 4 is connected to a check valve 35, thence to one arm 30 of a tubing tee 31. A second arm 32 of the tee 31 is connected to a second tube 33, which directs water to the mixer 7 for mixing with water from the hot water tube 3. To the third arm 34 of the tee 31 is connected a lower petcock 36 which allows a side stream of water to enter a soap tank 37 at inlet tap 38. An outlet tap 39 at the top of the soap tank 37 allows soapy water to flow via soap tube 40 to the inlet of soap control petcock 41. Watertight cap 42 on tank 37 allows soap to be added into the tank, or cleaning of the tank. The outlet of soap control petcock 41 may be attached directly to the outlet of mixer 7 (as shown) or it may be attached to (not shown) or built into (not shown) spray gun 11 so that the user can control soap application and water flow with one hand. In these latter cases, soap tube 40 is extended to the spray gun preferably by being attached alongside or wrapped around hose 10.

Figure 4:
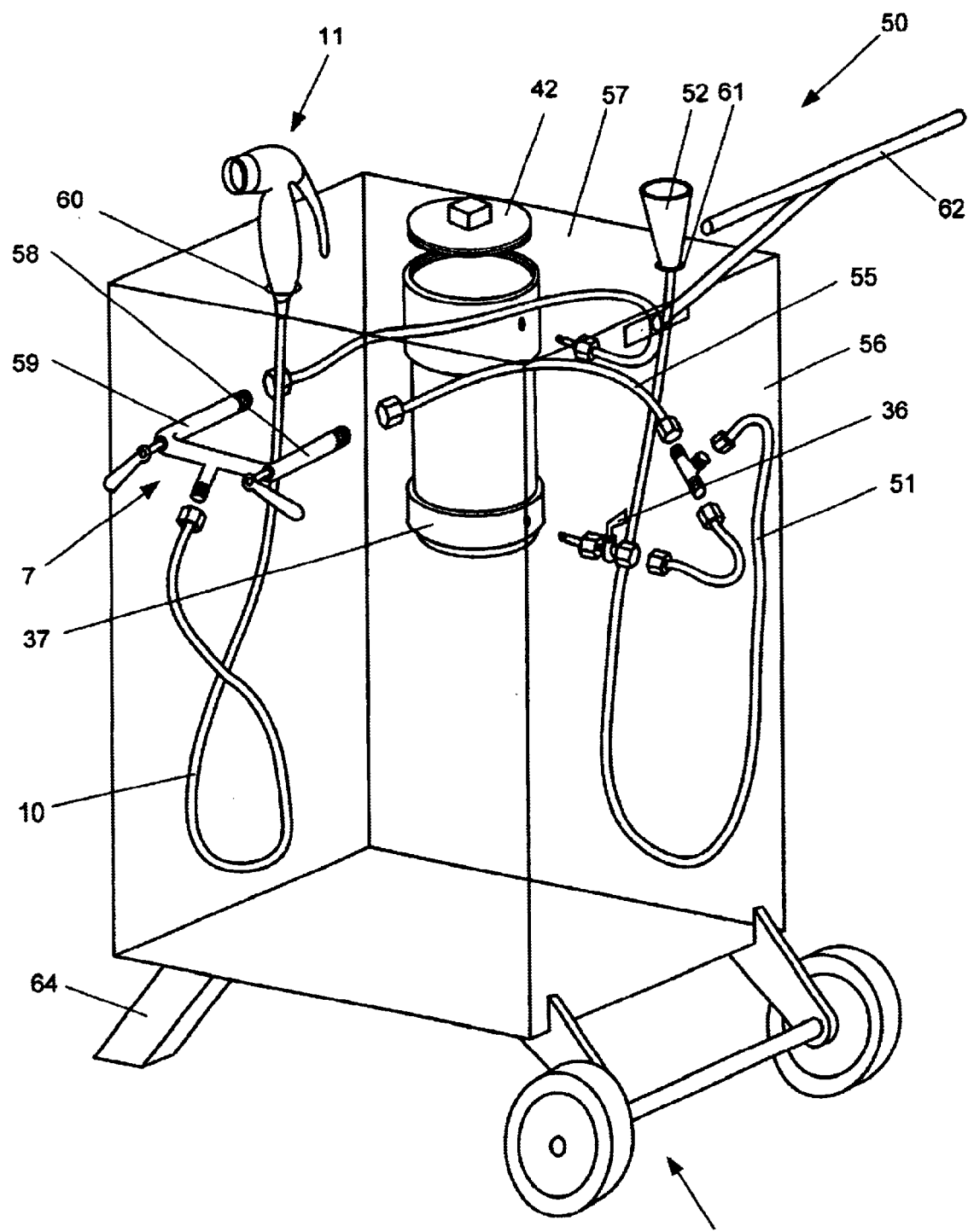
FIG. 4 is a perspective view of a fourth, portable, embodiment of the invention.

FIG. 4 is a perspective view of a fourth, portable, embodiment of the invention. In this illustration, it is embodied in a wheeled cart 50, although the same assembly could be fitted into a carrying case or other means of portage. The functional difference between this embodiment and the third embodiment is that there is only one water tube 51 instead of hot and cold water tubes 3 and 4 (not shown). A flexible funnel 52 is used to connect the apparatus to a sink or bathtub faucet (not shown) after the temperature of the water has been adjusted properly at the sink or faucet. The water from tube 51 flows to one arm of a tee 53, where it is split to a soap tank supply hose 54 and a fresh water supply hose 55. The soap tank supply hose 54 goes to a lower petcock 36 and thence to the soap tank 37. The soap tank 37 is mounted within cabinet 56 so that its watertight cap 42 may be opened at an accessible surface 57 of the cabinet 56. Cabinet 56 is shown here with rigid transparent walls so that components of the invention can be seen, but neither transparency nor rigidity of walls is a necessary aspect of the invention. The fresh water supply hose 55 goes to a mixer 7 where the flow of fresh water is controlled by a water valve 58. Soapy water leaves soap tank 37 via soap supply hose 40 to mixer 7 where its flow is controlled by soap valve 59. Mixed water leaves the mixer 7 via hose 10 to enter spray gun 11. Spray gun 11 is stored in recess 60 in surface 57 when not in use. Funnel 52 likewise is stored in hole 61 in surface 57 when not in use. When the invention is installed in a cart 50, typically the cart may comprise additionally a handle 62, wheels 63 and a foot 64 for ease of handling, but other means of portability including casters or a shoulder strap are not meant to be excluded by these depictions.

Figure 5:
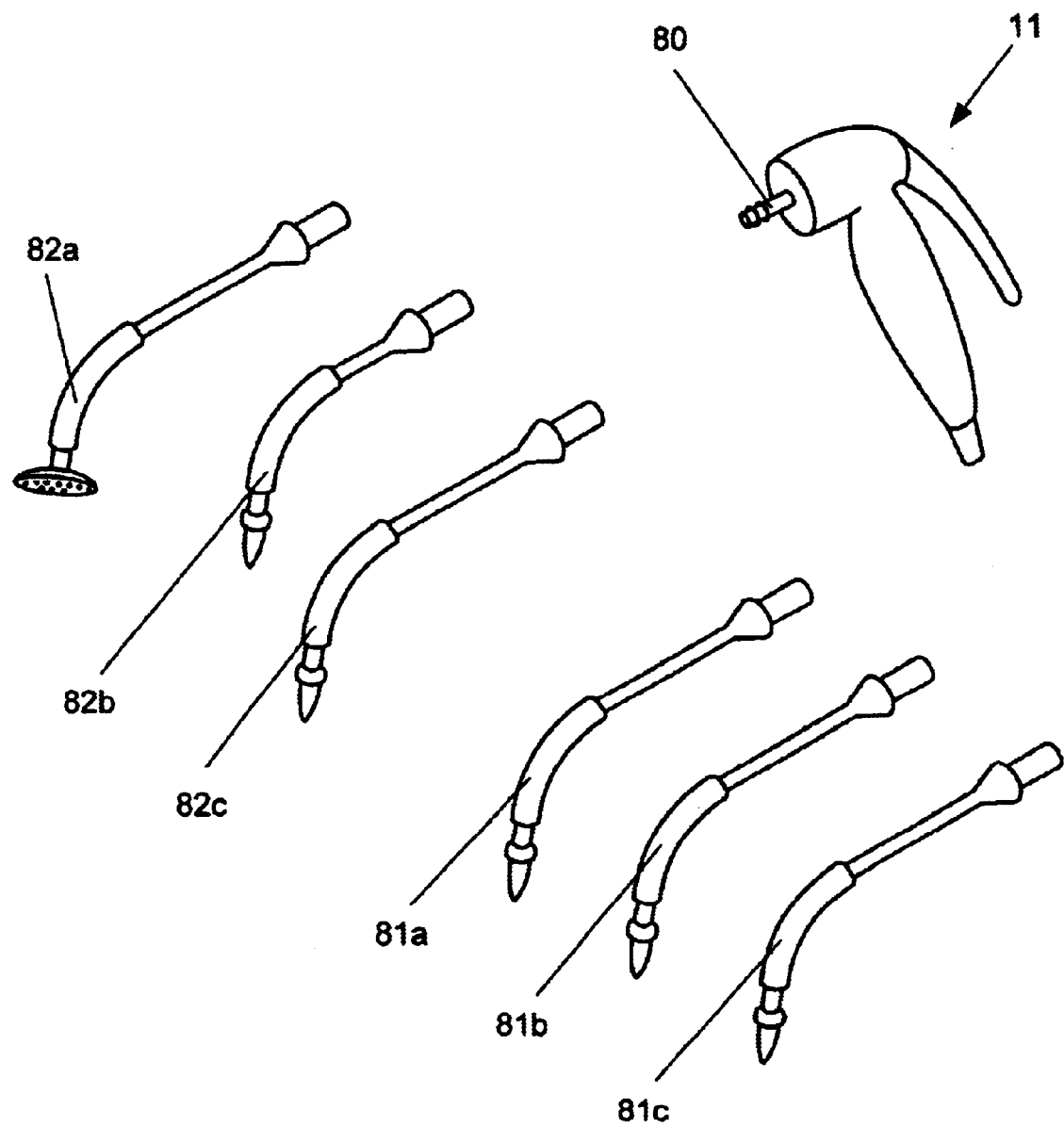
FIG. 5 is a perspective view of interchangeable spray heads for the invention.

FIG. 5 is a perspective view the spray gun 11 configured to receive detachable and interchangeable spray tips. This is a variation of the spray gun 11 portion of the invention in which the spray gun 11 does not have a built in spray tip, but instead a quick connect 80. Several spray heads of identical function but for different users 81*a*, 81*b*, and 81*c*, etc., or spray heads of different function (e.g, angles, spray patterns) 82*a*, 82*b*, and 82*c*, etc., can be connected to quick connect 80 as needed.

I claim:

1. The combination of a cleansing apparatus and an enclosure, the enclosure having a door and within the enclosure separate flexible supply tubes of pressurized hot and cold water, the apparatus being mounted on the inside surface of the door, wherein:

the apparatus comprises a hot water valve and a cold water valve, a flexible mixed water tube, a water spray head, and a bracket fixed to the inside surface of the door;

the hot and cold water supply tubes are connected to the inlets of the hot and cold water valves, respectively;

the outlets of the respective valves are joined together so as to mix the hot and cold water and feed it to the flexible mixed water tube;

the flexible mixed water tube passes through a hole in the bracket;

the mixed water tube delivers the mixed water to the spray head;

the spray head is held by the bracket when not in use; and the entire apparatus is accessible to use when the door is open and hidden in the enclosure when the door is closed.

2. The combination of claim 1, wherein:

said spray head further comprises a spring-biased normally-closed valve that opens when squeezed by hand.

3. The combination of claim 2, wherein:

said door is rectangular with a bottom edge and a top edge, hinged at the bottom edge and opening outward away from said enclosure at the top edge; and said valve and said bracket are fixed to said door near said top edge.

4. The combination of claim 3, further comprising:

a handle on the outside of said door;

means for latching the door in the closed position; and means for holding the door open at a fixed angle.

5. The combination of claim 4, wherein:

said enclosure is a bathroom vanity.

6. The combination of claim 5, wherein:

said spray head further comprises a tip, the tip being a rigid, angled, elongate tube.

7. The combination of claim 5, wherein:

said spray head further comprises a removable tip.

* * * * *